United States Patent [19]

Ryan et al.

[11] 4,448,715
[45] May 15, 1984

[54] TAGGED PYROGLU-L-PHE-L-ARG DERIVATIVES, SUBSTRATES AND ASSAYS FOR KALLIKREIN

[75] Inventors: James W. Ryan; Alfred Chung, both of Miami, Fla.

[73] Assignee: University of Miami, Miami, Fla.

[21] Appl. No.: 317,412

[22] Filed: Nov. 2, 1981

[51] Int. Cl.$^3$ .................... C07C 103/52; C12Q 1/56
[52] U.S. Cl. ............................ 260/112.5 R; 435/13
[58] Field of Search .................. 260/112.5 R; 435/13

[56] References Cited

U.S. PATENT DOCUMENTS

| | | | |
|---|---|---|---|
| 3,144,484 | 8/1964 | Erlanger | 260/562 |
| 3,536,588 | 10/1970 | Haschen | 195/103.5 |
| 3,591,459 | 7/1971 | Haschen | 195/103.5 |
| 3,607,859 | 7/1971 | Feder | 260/112.5 |
| 3,703,441 | 11/1972 | Nakanishi | 195/99 |
| 3,745,212 | 7/1973 | deBenneville | 424/9 |
| 3,769,173 | 10/1973 | Carroll | 195/103.5 R |
| 3,773,626 | 11/1973 | Bernt | 195/103.5 R |
| 3,862,011 | 1/1975 | Smith | 260/112.5 R |
| 3,884,896 | 5/1975 | Blomback | 260/112.5 |
| 3,886,136 | 5/1975 | Claeson | 260/112.5 |
| 3,892,631 | 7/1975 | Carroll | 195/99 |
| 4,016,042 | 4/1977 | Svendsen | 260/112.5 R |
| 4,028,318 | 6/1977 | Aurell | 260/112.5 R |
| 4,046,633 | 9/1977 | Keutel | 195/103.5 R |
| 4,056,519 | 11/1977 | Bobbitt | 260/112.5 R |
| 4,061,625 | 12/1977 | Kenstam | 260/112.5 R |
| 4,070,245 | 1/1978 | Svendsen | 260/112.5 R |
| 4,108,726 | 8/1978 | Silverstein | 195/103.5 R |
| 4,115,374 | 9/1928 | Ryan | 260/112.5 R |
| 4,116,774 | 9/1978 | Minato | 195/99 |
| 4,119,620 | 10/1978 | Nagatsu | 260/112.5 R |
| 4,137,225 | 1/1979 | Ekenstam | 260/112.5 R |
| 4,138,394 | 2/1979 | Sakakibara | 260/112.5 R |
| 4,147,692 | 4/1979 | Nagatsu | 260/112.5 R |
| 4,155,916 | 5/1979 | Smith | 260/345.2 |
| 4,162,941 | 7/1979 | Aurill | 260/112.5 R |
| 4,167,449 | 9/1979 | Gargiulo | 435/16 |
| 4,169,015 | 9/1979 | Ekenstam | 435/13 |
| 4,176,009 | 11/1979 | Sakakibara | 260/112.5 R |
| 4,177,109 | 12/1979 | Tohyama | 435/24 |
| 4,188,264 | 2/1980 | Iwanaga | 23/230 |
| 4,191,808 | 3/1980 | Nagatsu | 435/24 |
| 4,191,809 | 3/1980 | Nagatsu | 435/24 |
| 4,207,232 | 6/1980 | Claeson | 435/23 |
| 4,214,049 | 7/1980 | Ekenstam | 435/23 |
| 4,215,047 | 7/1980 | Sakakibara | 260/326.34 |
| 4,216,142 | 8/1980 | Ali | 260/112.5 R |
| 4,217,269 | 8/1980 | Cole | 260/112.5 R |
| 4,219,497 | 8/1980 | Plattner | 260/501.14 |
| 4,221,706 | 9/1980 | Ali | 260/112.5 R |
| 4,234,477 | 11/1980 | Fiedler | 260/112.5 R |
| 4,242,329 | 12/1980 | Claeson | 424/177 |
| 4,244,865 | 1/1981 | Ali | 260/112.5 R |
| 4,279,810 | 7/1981 | Claeson et al. | 260/112.5 R |
| 4,308,202 | 12/1981 | Fujii et al. | 260/112.5 R |
| 4,327,178 | 4/1982 | Ryan et al. | 260/112.5 R |

FOREIGN PATENT DOCUMENTS

WO80/00252 2/1980 PCT Int'l Appl. .......... 260/112.5 R
72057581 of 0000 Sweden .

OTHER PUBLICATIONS

Han, Y. N. et al., FEBS Letters 71, 45, (1976).
Fiedler, F. et al., Adv. Exp. Med. Biol. 120A, 261, (1978).
Amundsen, E. et al. (in Pisano, J. J. et al. eds), Chemistry and Biology of the Kallikrein-Kinn System in Health and Disease-U.S. Government Printing Office, (1976), p. 215.
Beaven et al., Clin. him. Acta 32, 67, (1971).
Claeson, G. et al., Haemostasis 7, 62, (1978).
Saito, H. et al., New England J. Med. 305, 910, (1981).
American Hospital Supply PCT/WO80/00351, (Not Supplied).
USSN 249,645, filed Mar. 31, 1981, (Not Supplied).
USSN 222,980, filed Jan. 7, 1981, (Not Supplied).
Boissonnas, R. S. et al., Helv. Chim. Acta 41, 1867, (1958).
Yoshimota et al., Biochim Biophys. Acta 569, 184, (1979).
Grant et al., Biochim. Biophys. Acta 567, 207, (1979).
Reilly et al., Biochim. Biophys. Acta 621, 147, (1980).
Pozgay et al., Eur. J. Biochem. 95, 115, (1979).
Lojda, Histochem. 64, 205, (1979).
Schroeder et al., Anal. Chem. 48, 1933, (1976).
Methoden der Organischen Chemie (Houben-Weyl), vol. XV, part II, (1974), (Book-Not Supplied).
Peptide Synthesis, Interscience Publishers, (1966), (Book-Not Supplied).
Biochemistry 4, 2509, (1965).
Aust. J. Chem. 20, 1493, (1967).
J. Am. Chem. Soc. 86, 4709, (1964).
J. Med. Chem. 20, 1176, (1977).
Nishi et al., Bull. Chem. Soc. Japan 43, 2900-2907, (1970).
Cornish-Bowden, A., Fundamentals of Enzyme-Kinetics, Butterworths London, (1979), p. 23.
Methoden der Organischen Chem. (Houben-Weyl), vol. XV, part I, pp. 376 et seq., (1974).
Iwanaga et al., Adv. Exp. Med. Biol. 120A, 147-163, (1978).
Bodansky, Peptide Synthesis, Interscience Publishers (1976).

Primary Examiner—Delbert R. Phillips

[57] ABSTRACT

Novel compositions of matter of the general formula

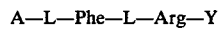

A—L—Phe—L—Arg—Y are described, in which A is lower alkanoyl, pyroglutamyl, substituted with —OH or halogen, and cyclo lower alkanoyls; Y is —OH or a known tag with either radioactive, fluorogenic, chromogenic or chemiluminescent properties.

The compounds of the invention are useful as novel substrates for plasma kallikrein.

A new method of performing the assay for plasma kallikrein is also described.

14 Claims, No Drawings

TAGGED PYROGLU-L-PHE-L-ARG DERIVATIVES, SUBSTRATES AND ASSAYS FOR KALLIKREIN

BACKGROUND OF THE INVENTION

The kallikreins (E.C. 3.4.21.8) are members of the family of pancreatic serine proteinases that includes trypsin, chymotrypsin, elastase, urokinase and plasmin. Kallikrein is capable of hydrolysing kininogen, having the partial amino acid sequence

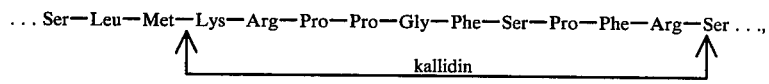

to yield kallidin, a decapetide with physiological properties similar to bradykinin. [Han, Y.N. et al. *FEBS Lett.* 71, 45 (1976); Fiedler, F. et al. *Adv. Exp. Med. Biol.* 120A, 261 (1978)]. Bradykinin is believed to act as a smooth muscle hypotensive agent.

| Table of Abbreviations | |
|---|---|
| Pro = | L-Proline |
| Phe = | L-Phenylalanine |
| Arg = | L-Arginine |
| Val = | L-Valine |
| Cpc = | Cyclopentane carbonyl |
| Leu = | L-Leucine |
| Pec = | 2-phenyl ethane carbonyl |
| Cbo = | Benzyloxy carbonyl |
| Bz = | Benzoyl |
| <glu = | L-pyroglu |
| HPK = | Human plasma kallikrein |
| HUK = | Human urinary kallikrein |
| Ser = | L-Serine |
| Met = | L-Methionine |
| Lys = | L-Lysine |
| Gly = | Glycine |
| BSA = | bovine serum albumin |
| pNA = | para-nitro anilide |

The present invention encompasses new compounds that act as unexpectedly potent substrates for plasma kallikreins. Sometime ago, applicants began a program to develop an assay for the kallikreins that combined the specificity of the chromogenic assay of Amundsen, E. et al. (in Pisano, J. J. et al. (eds.) *Chemistry and Biology of the Kallikrein —Kinin System in Health and Disease,* U.S. Government Printing Office 1976 p. 215) with the sensitivity of the radioassay of Beaven et al. (*Clin. Chim. Acta,* 32, 67 (1971). It had been shown that D—Pro—Phe—Arg—pNA is more reactive with plasma kallikrein than is Pro—Phe—Arg—pNA [Claeson, G. et al *Haemostasis* 7, 62 (1978)]. Applicants discovered that D—Pro—Phe—Arg—[³H]—benzylamide is less reactive with plasma kallikrein than is Pro—Phe—Arg—[³H]—benzylamide, indicating that it is not possible to predict the effects of changing leaving groups.

Applicants then began a search for amino acid residues (and related acyl groups) that might be used to replace Pro or (D)Pro in order to enhance the affinity of substrate for plasma kallikrein. Of twelve acyl groups thus surveyed, <Glu (5—keto—L—Pro) proved to be the best. <Glu—Phe—Arg—[³H]benzylamide is highly reactive with human plasma kallikrein. The results of applicants indicate that subtle changes in the side-chain of the P₃ (or proline) subsite of tripeptide substrates for the kallikreins can confer profound changes in selectivity and kinetic behavior.

Because of the role of kallikrein in regulation of blood pressure and renal blood flow, determination of kallikrein levels, particularly levels of active enzyme by hydrolysis of a substrate, is clearly relevant to clinical evaluation of disease. An assay for plasma kallikrein would be useful for screening patients for asymptomatic clotting defects, [Saito, H. et al. *New Engl. J. Med.* 305, 910 (1981)].

A variety of U.S. patents described substrates for proteolytic enzymes, some related to the kallikreins. See inter alia, U.S. Pat. Nos. 3,884,896; 4,016,042; 4,115,374; 4,137,225; 4,214,049; 4,215,047; 4,234,477; 4,242,329. See also American Hospital Supply PCT W080/00351, and applicants' pending application, U.S. Ser. No. 249,645 filed Mar. 31, 1981 which is a continuation of their application Ser. No. 34930 filed May 1, 1979. None of these references discloses the compounds of this invention as compositions of matter nor as substrates for plasma kallikrein. They do not describe the method of this invention for assaying plasma kallikrein.

For example, U.S. Pat. No. 3,886,136 discloses several chromogenic substrates for assaying enzymes of the class E.C. 3.4.4 (now class E.C. 3.4.21). Examples of this class include trypsin (E.C. 3.4.31.4), chymotrypsin (E.C. 3.4.31.1), plasmin (E.C. 3.4.21.7) and thrombin (E.C. 3.4.21.5), among others. The substrates disclosed in this patent have the general formula:

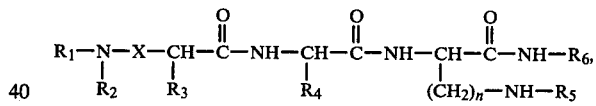

wherein R₃ and R₄ are alkyl groups having 3-8 carbons, R₄ can also be benzyl or phenyl, R₅ is hydrogen or

n is 2, 3 or 4, —NH—R₆ is the chromogenic group, X is CH₂ or a single bond, and R₁ and R₂ can be selected from a variety of groups which is not critical to this discussion. U.S. Pat. No. 4,016,042 discloses chromogenic or fluorogenic substrates for proteolytic enzymes of the class E.C. 3.4.31. These substrates are derivatives of Pro—X—Y—R where X is Phe, Tyr, phenylglycine or β-cyclohexylalanine, Y is Arg or Lys and R is the chromogenic or fluorogenic group.

U.S. Pat. No. 4,137,225 discloses chromogenic substrates for proteases (serine proteases) of the class E.C. 3.4.21. This patent discloses substrates of the formula (D)A₁—A₂—A₃—R where A₁ and A₂ are selected from the group of amino acids Gly, Ala, Val, Leu, Ile, Pip, Pro or Aze, A₂ can also be Phe, A₃ is Arg, Lys or Orn and R is the chromogenic group.

Other U.S. patents which disclose chromogenic or fluorogenic peptide substrates include the following: U.S. Pat. No. 3,144,484 for trypsin (E.C. 3.4.31.4); U.S. Pat. No. 3,536,588 for Leu aminopeptidase (E.C.

3.4.11.1); U.S. Pat. No. 3,591,459 for amino acid arylamidase; U.S. Pat. No. 3,607,859 for neutral protease (microbial metalloenzymes, E.C. 3.4.23.4 ); U.S. Pat. Nos. 3,703,441; 3,769,173; 3,773,626; 3,892,631 and 4,177,109 for γ-Glu transpeptidase (E.C. 2.3.2.2); U.S. Pat. No. 3,745,212 for pancreatic endopeptidases; U.S. Pat. Nos. 3,884,896, 4,191,808 and 4,191,809 for peptide peptidohydrolases such as class E.C. 3.4.21; U.S. Pat. No. 4,046,633 for renin (E.C. 3.4.99.19); U.S. Pat. Nos. 4,108,726 and 4,115,374 for angiotensin converting enzyme (peptidyldipeptide hydrolase, E.C. 3.4.15.1); U.S. Pat. No. 4,116,774 for Leu aminopeptidase, Cys aminopeptidase (1E.C. 3.4.11.3) and γ-Glu transpeptidase; U.S. Pat. No. 4,138,394 for collagenase (E.C. 3.4.24.3); and U.S. Pat. No. 4,207,232 for factor Xa (E.C. 3.4.21.6).

The present invention encompasses novel derivatives of <Glu—Phe—Arg—Y as new compositions of matter, wherein the indicator Y is either a radioactively tagged group, or a tag with fluorogenic, chromogenic or chemiluminescent properties. The compounds are unexpectedly effective substrates for plasma kallikrein. In addition, the method of assaying plasma kallikrein in this invention is novel.

BRIEF DESCRIPTION OF THE INVENTION

This invention relates to novel compounds of the general formula:

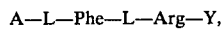

A—L—Phe—L—Arg—Y, or methyl esters thereof or ethyl esters thereof, wherein, group A contains a carbonyl group in amide linkage with the α-amino group of L—phe, and is cyclopropanecarbonyl, cyclobutanecarbonyl, cyclopentanecarbonyl, cyclohexanecarbonyl, pyroglutamyl, 3,4-dehydroprolyl, 4-ketoprolyl, 4-OH-prolyl, 3-OH-prolyl, 3-phenylpropanoyl, thioprolyl, azetidine-2-carbonyl, thiazolidine-4-carbonyl, 5-X-prolyl, 4-X-prolyl, 3-X-prolyl, or 2-X-prolyl wherein X of any of the last four radicals is halo;

Y is joined to the α-carbonyl of L—Arg and is —OH or any one of the indicators consisting essentially of a radioactively tagged group, a chromogenic tag, a fluorogenic tag and a chemiluminescent tag; when Y is any of said indicators, Y forms either an ester linkage with L—arg or an amide linkage with L—arg.

This invention also encompasses a method for the quantitative determination of plasma kallikrein which comprises contacting said kallikrein with substrate compound having the following general formula:

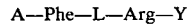

A—Phe—L—Arg—Y group A contains a carbonyl group in amide linkage with the α-amino group of L—Phe, and is cyclopropanecarbonyl, cyclobutanecarbonyl, cyclopentanecarbonyl, cyclohexanecarbonyl, pyroglutamyl, 3,4-dehydroprolyl, 4-ketoprolyl, 4-OH-prolyl, 3-OH-prolyl, 3-phenylpropanoyl, thioprolyl, azetidine-2-carbonyl, thiazolidine-4-carbonyl, 5-X-prolyl, 4-X-prolyl, 3-X-prolyl, or 2-X-prolyl wherein X of any of the last four radicals is halo;

Y is joined to the α-carbonyl of L—Arg and is —OH or any one of the indicators consisting essentially of a radioactively tagged group, a chromogenic tag, a fluorogenic tag and a chemiluminescent tag; when Y is any of said indicators, Y forms either an ester linkage with L—arg or an amide linkage with L—arg;

incubating the kallikrein with the substrate compound to permit detectable kallikrein-catalyzed hydrolysis;

separating the hydrolysis product from the substrate compound, and measuring the amount of product formed by measuring the tag thereof, whereby an assay for plasma kallikrein is obtained.

DETAILED DESCRIPTION OF THE INVENTION

The present invention in its broad aspects relates to new compositions of matter useful as novel substrates for kallikrein and related proteases, particularly plasma kallikrein. These substrates are derivatives of Phe—Arg, having the general formula:

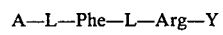

A—L—Phe—L—Arg—Y wherein A is an acyl group and Y is —OH or is an indicator such as, e.g., a radioactively tagged group, a chromogenic tag, a fluorogenic tag or a chemiluminescent tag. The A group is in amide linkage with phenylalanine. Phenylalanine is linked to arginine by a peptide bond. The α-carbonyl of arginine is linked to the indicator group.

The A group encompasses cyclopropanecarbonyl, cyclobutanecarbonyl, cyclopentane carbonyl, cyclohexane carbonyl, pyroglutamyl, halogenated derivatives of prolyl, unsaturated derivatives of prolyl, keto derivatives of prolyl, hydroxy derivatives of prolyl, thioprolyl, azetidine-2-carbonyl thiazolidine-4-carbonyl, 3-phenyl propanoyl, other α-amino alkanoyls, phenyl α-amino alkanoyls, α,α-diamino alkanoyls, and alkanoyls.

The A group is preferably pyroglutamyl, 3-phenyl propanoyl, or 4-keto-prolyl. Most preferably, the A group is pyroglutamyl.

It is understood that L—Phe and L—Arg represent the L optical isomers of phenylalanine and arginine, respectively.

The Y indicator can be a radioactively tagged group, or a fluorogenic tag, a chromogenic tag or a chemiluminescent tag. All of these indicators form either an amide linkage or an ester linkage with L—arginine such that these linkages are cleavable by the enzyme. It is to be understood that the invention also encompasses compounds of the formula A—L—Phe—Arg—Y wherein Y is —OH, i.e., one of the two presumed products of the reaction of substrate and enzyme.

When Y is a radioactively tagged group it can be either a [$^{14}$C] or a [$^{3}$H] label in anilino, benzylamino, or lower alkoxy; or a halo label in hydroxy anilino, naphthylamino, hydroxybenzylamino or coumaryl-7-amino. Preferably, Y as a radioactively tagged group is either a [$^{14}$C] or a [$^{3}$H] label in anilino or benzylamino; most preferably it is [$^{3}$H]-benzylamino.

When Y is a chromogenic tag, it can be p—NO$_2$-anilino, p—NO$_2$-phenyloxy, nitrophenylamino, naphthylamino, nitronaphthylamino, methoxynaphthylamino, quinolylamino, nitroquinolylamino, 4-trifluoromethyl coumaryl-7-amino, or naphthylamino tagged with radioactive halogen. Preferably Y as a chromogenic tag is p—NO$_2$-anilino or 2-naphthylamino.

However, when Y is a fluorogenic tag, it can be 4-methyl coumaryl-7-amino, 4-trifluoromethyl coumaryl-7-amino, naphthylamino, 7-oxy-coumaryl, 5-amino isophthalic acid diethyl ester, coumaryl-7-amino tagged with radioactive halogen, or $^3$H, or naphthylamino tagged with radioactive halogen or $^3$H. Most preferably, Y as a fluorogenic tag is 4-methyl-coumaryl-7-amino or 4-trifluoromethyl coumaryl-7-amino.

Alternatively, Y can be a chemiluminescent tag such as amino-isoluminol.

The radioactively tagged groups of this invention can be synthesized by a variety of techniques. The synthesis of [$^3$H] benzylamide tagged substrates for urinary kallikrein is disclosed in applicants' co-pending U.S. application, Ser. No. 222,980, filed Jan. 7, 1981. [$^{14}$C]-ethanol or [$^3$H] ethanol are commercially available, and techniques for esterification of a free carboxy terminus of an amino acid are well known, e.g., refluxing ethanol and amino acid in the presence of thionyl chloride. See U.S. Pat. No. 4,234,477 and Boissonnas, R. S. et al. *Helv. Chim Acta* 41, 1867 (1958). Compounds of the formual A—L—Phe—Arg-1-amino-4-bromo-naphthalene can be tagged to form radioactive substrates, e.g., A—L—Phe—L—Arg-1-amino-4-[$^{125}$I]-naphthalene, by halogen exchange. Similarly, A—L—Phe—L—Arg-2-amino-4-bromo-naphthalene can be tagged to form its corresponding radioactively tagged substrate by halogen exchange. Tritiated naphthalene as a Y indicator can be synthesized by catalytic hydrogenation of amino naphthalene, preferably done before coupling with the α-carbonyl of L—Arg. It will be understood that, in connection with the synthesis of radioactively tagged groups attached in amide or ester linkage with the α-carbonyl of L—Arg in A—L—Phe—L—Arg, the invention is capable of further modifications, and this application is intended to cover any variations, uses or adaptations thereof, including such departures from the present disclosure as are known to one of ordinary skill in the art of synthesizing radioactively tagged groups.

Numerous patents and literature references have described chromogenic and fluorogenic substrates, some of which are themselves cleaved off during reaction with enzyme. See, inter alia U.S. Pat. Nos. 3,884,896; 3,886,136; 4,016,042; 4,028,318; 4,119,620; 4,147,692; 4,155,916; 4,191,808; 4,191,809 4,207,232; and 4,167,449 which contain lists of specific chromogenic or fluorogenic substrates for various proteolytic enzymes. Still further colorimetric substances useful for assaying one or more of thrombin, horseshoe crab coagulating enzyme, urokinase or Factor XIIA are shown in U.S. Pat. No. 4,215,047. Further substrates for thrombin and trypsin-like enzymes are shown in U.S. Pat. Nos. 4,217,269, 4,210,497 and 4,221,706. U.S. Pat. No. 4,216,142 describes substrates especially useful with the enzyme inhibitor anti-thrombin III.

In addition to the above-identified U.S. patents, chromogenic or fluorogenic peptide substrates for various proteolytic enzymes have also been described in many literature articles. Representative articles include the following: Yoshimota et al., *Biochim. Biophys. Acta*, 569, 184 (1979) for post-proline cleaving enzyme (E.C. 3.4.31.-) using Z—Gly—Pro-R$_1$ wherein R$_1$ is a chromogenic or fluorogenic group as the substrate; Grant et al., *Biochim. Biophys. Acta* 567, 207 (1979) for enterokinase (E.C. 3.4.21.9) using Gly—(Asp)$_4$—Lys-naphthylamide; Reilly et al., *Biochim. Biophys. Acta* 621, 147 (1980) for elastase (E.C. 3.4.31.11) using succinyl-(ala)$_3$-p-nitroanilide; Pozgay et al., *Eur. J. Biochem* 95, 115 (1979) for Subtilisin Carlsberg (E.C. 3.4.21.14) using, for example, Z—Arg—(Nle)$_2$—p-nitroanilide; and Lojda, *Histochem.* 64, 205 (1979) for brush border endopeptidase using glutaryl-(ala)$_3$-MNA or succinyl-(ala)$_3$-1-naphthylamide.

The Y group can also be a chemiluminescent group, such as amino-isoluminol [Schroeder et al. *Anal. Chem.* 48, 1933 (1976)].

The linkage group between L—Arg and the indicator Y in A—L—Phe—L—Arg—Y of this invention can be either an amide structure with the α-carbonyl of arginine joined to the amino function of Y, or, secondly an ester group with the α-carbonyl of arginine joined to the oxy atom of Y. When an amide structure is involved, methods for synthesis of L—arg—Y structure in A—L—Phe—L—Arg—Y of this invention are the same as traditional coupling methods of peptide synthesis. On the other hand, the ester linkage between L—Arg and Y can be formed by standard techniques in organic chemistry, e.g., esterification in the presence of mineral acids or in the presence of thionyl chloride. Generally, the formation of acid halides of L—arg is not preferred because of racemization.

The compounds of this invention can be synthesized by any of the conventional coupling methods of peptide synthesis, which are commonly named after the coupling agents used. Examples of agents used in conventional coupling methods include: 1,1'-carbonyldiimidazole (CDI), dicyclohexylcarbodiimide (DCC), mixed anhydride (MA), N-ethyloxycarbonyl-2-ethyloxy-1,2-dihydroquinoline (EEDQ), N-isobutyloxycarbonyl-2-isobutyloxy-1,2-dihydroquinoline, symmetrical anhydride, Woodward's reagent K (N-ethyl-5-phenylisoxazolium-3'-sulfonate), ethoxyacetylene or diphenylphosphoryl azide. For reviews of these coupling methods, see *Methoden der Organischen Chemie* (Houben-Weyl) Vol. XV, part II, p. 1 et seq. (1974), and *Peptide Synthesis*, Interscience Publishers (1966).

Conventional coupling methods include the following: The carboxylic acid of either the A group, phenylalanine or arginine can first be coupled with N-hydroxysuccinimide then reacted with phenylalanine, arginine or Y, respectively, to yield A—Phe, Phe—Arg, or Arg—Y, respectively. Alternatively, the carboxylic acid can be coupled with a t-butyl ester of the reactive pair by the MA method, producing the appropriate t-butyl ester, which can be deprotected with TFA. A third alternative is to react the acylhalide with the appropriate amino group, but this is less preferable because of racemization.

One well known synthetic route for the compounds of this invention is to couple Nα,Nω-protected arginine to the indicator and then couple group A and Phe to the product in step-wise fashion. For example, a benzylamide compound is attached to the C-terminal amino acid group. The benzylamide group at the same time protects the C-terminal carboxyl group during the step-wise attachment of the amino acids in the process of building up the peptide chain. The other protecting groups are selectively eliminated from the end product without the benzylamide group being affected.

Alternatively, one can couple the Y group to A—L—Phe—L—Arg. Typically, a benzylamino group can be coupled to the finished peptide chain before the protecting groups, if any, are removed.

Suitable protecting groups for free amino or free carboxyl groups are well known. For example, during coupling of arginine to the indicator group the α-amino group of arginine can be protected by t-butyloxycarbonyl (Boc), but it can be replaced with any acid sensitive amino protecting group such as 2-(4-biphenyl)-2-propyloxycarbonyl (Bpoc), 2-phenylisopropyloxycarbonyl (Ppoc), benzyloxycarbonyl (Cbo) or other acid sensitive N-aralkyloxycarbonyl protecting group.

Deprotection, that is, removal of the protecting group, can be effected by any conventional means such as trifluoroacetic acid (TFA) in anisole, HBr in acetic acid, cold trifluoromethane sulfonic acid and methanolic ammonia. See *Methoden der Organischen Chemie* (Houben-Weyl) Vol. XV, part I, p. 376 et seq. (1974).

The C-terminal carboxy group in the peptide derivatives can be protected during the stepwise synthesis of the required peptide chain by means of a benzylamide group or by conversion into the methyl, ethyl or tert-butyl ester.

The other active free groups which do not participate in the synthesis of the peptide chain can be blocked by known methods. Thus, the ω-guanidino group of arginine may be protected by $NO_2$ or Tos or a salt.

The synthesis of the compounds of this invention is simplified by the commercial availability of a variety of intermediates, such as Nα—Boc—L—Arg—HCl, L-phenylalanyl-L-arginine, L-arginine-4-methyl coumaryl-7-amide, all from Chemical Dynamics Corp., South Plainfied, N.J. Other standard chemical and biochemical supply companies include Aldrich Chemical Company, Inc., Metuchen, N.J. and Sigma Chemical Company, St. Louis, Mo.

The halogenated prolines of group A can be produced by methods known in the art. See, for example, *Biochem.* 4; 2509 (1965); *Aust. J. Chem.* 20; 1943 (1967); *J. Am. Chem. Soc.* 86; 4709 (1964); and *J. Med. Chem.* 20; 1176 (1977).

The compounds of this invention have one or more asymmetric carbons. The compounds accordingly exist in stereoisomeric forms or in racemic mixtures thereof. The above described syntheses can utilize a racemate or one of the enantiomers as starting material. When the racemic starting material is used in he synthetic procedure or a racemic mixture results from the synthesis, the stereoisomers obtained in the product can be separated by conventional chromatographic or fractional crystallization methods. The most preferred stereoisomer of this invention is A—L—Phe—L—Arg—Y. When A is pyroglutamyl, A can be the L or D isomer, or racemic mixture thereof.

The compounds of the present invention have been discovered to be excellent substrates for human plasma kallikrein. For example, <Glu—L—Phe—L—Art-[$^3$H]-benzylamide, the most preferred substrate, has a $K_m$ of 6 μM and $K_{cat}$ of 35.5 min.$^{-1}$ with a substrate concentration within the range of $10^{-7}$ M to $2.6 \times 10^{-5}$ M. The low $K_m$ renders this substrate and others especially suitable for an enzyme assay, and sensitivity is maximized when the substrate has a high specific radioactivity. The specific radioactivity is a function of the proportion of labelled to unlabelled molecules in the substrate preparation. Generally, the cost of the substrate preparation will increase as the specific radioactivity is increased. Therefore, substrates that can be used at low concentration, such as those of the present invention, are advantageous. The low $K_m$ values exhibited by the substrates of the present invention are indicative of a highly specific binding between the enzyme and substrate. Such specific binding generally increases the likelihood that substrate will only be hydrolyzed by human plasma kallikrein rather than some other enzyme with trypsin-like activity, especially when substrate is present in relatively small amounts in the assay mixture.

It is preferable to conduct the enzyme assay of this invention such that first order enzyme kinetics are obeyed. The preferable substrate concentrations may range from about $2K_m$ to about $10^{-4}K_m$ for most indicator groups. Substrate concentrations may go down to about $5 \times 10^{-7} K_m$ for indicator groups of high specific activity, such as any [$^{125}$I] or [$^{131}$I] labelled group of the invention.

A novel feature of the enzyme assay for human plasma kallikrein in this invention is the addition of enough carrier protein to the sample buffer to prevent what is thought to be non-specific absorption of human plasma kallikrein to the walls of the reaction vessel, also called "plating out". Applicants have found that a concentration above about 2 mg/ml is effective in substantially eliminating this apparent effect. The range of concentration of the carrier is between about 2 mg/ml to about 100 mg/ml, preferably between about 2 mg/ml and about 10 mg/ml. The most preferred concentration is about 4 mg/ml.

Additional experimental details are found in the examples which are preferred embodiments and also serve as models for the preparation of other members of the group.

The present invention is further described by the following examples. All temperatures are in degrees Celsius unless otherwise indicated. Molar equivalents of the reactants are usually utilized.

EXAMPLE 1

Synthesis of <Glu—Phe—Arg-[$^3$H]-benzylamide.HCl

A. Synthesis of Boc—Arg ($NO_2$)-4-bromo-benzylamide

A solution of 20 mmoles of Boc—Arg ($NO_2$)—OH in 25 ml of redistilled DMF was cooled to $-20°$ C. To this solution was added 20 mmoles (2.72 ml) of N-ethyl morpholine and then 20 mmoles of isobutylchloroformate (2.64 ml). The solution was stirred for 5 minutes at $-15°$ C. and then a suspension of 4-bromo-benzylamine-HCl, neutralized with 2.72 ml of N-ethylmorpholine, in 20 ml of DMF (dimethylformamide) was added. The reaction mixtures was stirred at $-15°$ C. for 1.5 hours, warmed to room temperature and stirred for 3 more hours. Solvent was removed in a rotary evaporator at 35° C. The residue was taken up in 150 ml of ethyl acetate. The organic phase was washed until neutral, THF (tetrahydrofuran) was added to break emulsions. The washed organic phase was dried over anhydrous $MgSO_4$ and was filtered. Solvent of the filtrate was removed with a rotary evaporator to yield a clear oil. The product of step A was crystallized from methanol and ether to yield 6.84 g (70.2% yield) of a white glassy solid. Elemental analysis for $C_{18}H_{27}N_6BrO_5$, FW 487.365 Calc: C 44.36, H 5.58, N 17.24, Br 16.4. Found: C 44.39, H 5.64, N 16.68, Br 16.48. The product behaved as a single substance on thin layer chromatography.

B. Preparation of 2 HCl—Arg-4-bromobenzylamide

The product of step A, 4.5 mmol, was treated with 2.2 ml of anisole and 25 ml of anhydrous HF at 0° C. for 2 hours. After removal of HF, the compound was dried over NaOH pellets in a vacuum desiccator overnight. The material was dissolved in $H_2O$, 60 ml, and was extracted several times with ether to remove anisole.

Hydrochloric acid, 9 mmoles, was added and then solvent was removed with a rotary evaporator. The residue was dissolved in 8.5 ml of 1 M HCl, and solvent was removed again under vacuum to yield a yellow gum. The solid material was triturated with ether to yield a white solid, which was collected by filtration and washed with ether. 2 HCl.Arg-4-bromo benzylamide was obtained dry after 16 hours in a vacuum desiccator (over NaOH pellets).

C. Synthesis of Boc—Phe—Arg-4-bromo-benzylamide

Boc—Phe-2-$NO_2$-phenyl ester (3.5 mmol) was added to a solution of 3.67 mmol of Arg-4-bromo-benzylamide.2HCl in 8 ml of redistilled DMF and 0.41 ml of N-ethyl morpholine, all at room temperature. The mixture was stirred overnight and then the solvent was removed by rotary evaporation. The residue was suspended in 20 ml of ethyl acetate plus 1 ml of acetic acid. The lower phase was separated and was washed with ethyl acetate. The organic phases were combined, mixed with 3 ml of acetic acid, and the mixture was stirred for 3 hours at room temperature. The organic phase was washed three times with saturated NaCl, dried over anhydrous $MgSO_4$ and then filtered. Solvent was removed with a rotary evaporator to yield yellow crystals of the product of step C.

D. Synthesis of 2 HCl. Phe—Arg-4-bromo-benzylamide

The product of step C was deprotected with 30 ml of 4.5 M hydrogen chloride in ethyl acetate at 4° C. for 1 hour and then at room temperature for 1 hour. Solvent was removed with a rotary evaporator to yield faint yellow crystals. The crystals were collected by filtration, washed with ethyl acetate and then dried in a vacuum desiccator over $P_2O_5$ and NaOH. Yield 1.49 g (75.6) of white crystals. The desired product was recrystallized from ethanol and a few drops of $H_2O$. A second crystallization was achieved from ethanol, $H_2O$ and benzene (0.46 g of white needles, d.p. 252°–253° C.). More of the product of step D was recovered from the mother liquid by chromatography on Bio-Rex 70 (1.1×70 cm column) developed first with $H_2O$ and then with 10% acetic acid. The material eluted with 10% acetic acid and was further purified on Sephadex G-10 (1.2×99 cm column) developed with $H_2O$ (yield 320 mg). Elemental analysis for $C_{22}H_{31}N_6O_2BrCl_2$, FW 562.347: Calc: C 46.99, H 5.56, N 14.94, Br 14.21, Cl 12.61. Found: C 47.10, H 5.50, N 14.90, Br 13.83, Cl 12.74. Amino acid analysis: Phe 1.01, Arg 1.00.

E. Preparation of 2 HCl.Phe—Arg-[$^3$H]benzylamide

The product of step D, 10.35 mg (18.4 μmol) was dissolved in 2 ml of DMF/$H_2O$ (1:1 by volume) and was reacted at room temperature with 10 mg of 10% Pd on $CaCO_3$ and 10 Ci of $^3H_2$ gas for 3 hours. The named compound was obtained by filtration to remove the catalyst and by repeated lyophilization from $H_2O$ and methanol. Specific radioactivity: 21.7 Ci/mmole F. Synthesis of <Glu—Phe—Arg-[$^3$H]benzylamide.HCl The product of step E, 1 mCi (0.045 μmol) was reacted with 2 equivalents of <Glu-trichlorophenyl ester in 0.2 ml of redistilled DMF at room temperature overnight. The reaction mixture was applied to a column (1.1×90 cm) of Bio-Gel P-2 developed with 10% acetic acid. The radioactive fractions were combined, and solvent was removed by lyophilization. The product behaved as a pure substance in three thin layer chromatography systems and was indistinguishable from <Glu—Phe—Arg-[$^3$H]benzylamide (see example 2).

EXAMPLE 2

Synthesis of <Glu—Phe—Arg-benzylamide.HCl

Phe—Arg-4-bromo-benzylamide, 0.1 mmol, was dissolved in 0.2 ml of redistilled DMF and 0.1 mmol (0.014 ml) of triethylamine. To this solution was added 0.11 mmol of <Glu-trichlorophenyl ester in 0.2 ml of DMF, and the resulting solution was stirred at room temperature overnight. The reaction was judged to be complete by thin layer chromatographic analysis. Solvent was removed under high vacuum at 40° C. The residue was dissolved in a small amount of 10% acetic acid, and the solution was applied to a column of Sephadex G-10 (1.2×99 cm) developed with 10% acetic acid. Fractions, 3.7 ml/fraction, were collected. Fraction, 28–33 were pooled (47 mg of dry weight), and the material was rechromatographed on Sephadex G-25 developed for partition chromatography (butanol/acetic acid/-$H_2O$; 4:1:5 by volume). The product, 43 mg, was analyzed for its amino acid content: Glu 1.02, Phe 0.995, Arg 1.00. 5 mg was submitted to catalytic dehalogenation in $^1H_2$ gas: 0.8 ml of DMF/$H_2O$ (1:1 by volume), 5 mg of 10% Pd on $CaCO_3$, $H_2$ gas at 1 atmos., stir at room temperature for 2 hours. The catalyst was removed by filtration and solvent was removed from the filtrate by rotary evaporation under high vacuum at 40° C. The named compound behaved as a pure substance by three chin layer chromatography systems and by paper electrophoresis at pH 5.0 and 1.9.

EXAMPLE 3

Synthesis of <Glu—Phe—Arg-4-$NO_2$-anilide

A. Preparation of Arg($NO_2$)-4-$NO_2$-anilide.HBr

Nα—Cbo—Arg($NO_2$)-4-$NO_2$-anilide is prepared according to the procedure of Nishi et al. (*Bull. Chem. Soc. Jpn.* 43, 2900–2907, 1970). The product of step A of Example 3 is obtained by removing the Cbo-group with HBr in acetic acid (2 hours at room temperature). The named compound is crystallized from $H_2O$ and then dioxane.

B. Preparation of Boc—Phe—Arg($NO_2$)-$NO_2$-anilide

The product of step A of Example 3, 4.2 g, and 1.29 ml of N-ethyl-morpholine in 10 ml of DMF are mixed with stirring with 3.62 g of the N-OH-succinimide ester of Boc-Phe in 5 ml of dioxane, all at 0° C. After one hour at 0° C., the solution is stirred at room temperature overnight. Solvent is removed under vacuum. Ether, 30 ml, is added. The organic phase is washed until neutral, dried over $MgSO_4$ and then filtered. Solvent of the filtrate is removed under vacuum. The desired compound is obtained by crystallization from ethyl acetate and hexane.

C. Preparation of <Glu—Phe—Arg-4-$NO_2$-anilide

The product of step B of Example 3, 5 g, is treated with 30 ml of 4.5 M hydrogen chloride in ethyl acetate at 4° C. for one hour and then at 22° C. for 30 minutes. Solvent is removed under reduced pressure. The residue is washed with anhydrous ether and then dried in a vacuum desiccator. The resulting product, 0.523 g, plus 0.129 ml of N-ethyl-morpholine in 2 ml of DMF are mixed with 0.308 g of <Glu-trichlorophenyl ester in 2 ml of DMF. The mixture is stirred at 22° C. overnight. After removal of solvent, the product is crystallized from ethyl acetate and ether. The crystals are treated with 2 ml of HF in the presence of 0.2 ml of anisole at 0° C. for one hour. HF and anisole are removed under vacuum, and the desired compound is obtained pure by column chromatography on Sephadex G-10 developed with 25% acetic acid.

EXAMPLE 4

Preparation of 2-(<Glu—Phe—Arg)-Naphthylamide

A. Preparation of 2-(Nα-carbobenzoxy-L-arginyl)-naphthylamide

DCC, 10.5 g, in 10 ml of DMF is added to a solution of 34.5 g of Nα—Cbo—L—Arg—HCl, 7.16 g of 2-aminonaphthalene and 7.7 g of 1-hydroxybenzotriazole monohydrate in 150 ml of DMF at 0° C. The mixture is stirred at 0° C. for 2 hours and then at 4° C. for 2 days. Solid DCCU (dicyclohexylurea) is removed by filtration and is washed with DMF. Solvent of the filtrates is removed under reduced pressure. The residue is crystallized from methanol/benzene, yielding the desired compound.

B. Preparation of <Glu—Phe-trichlorophenyl ester

Hydrogen chloride, 4.5 M in ethyl acetate, (40 ml) is added to a stirred solution of Boc—Phe-trichlorophenyl ester in 15 ml of ethyl acetate at 0° C. The mixture is stirred at 0° C. for 10 minutes and then at room temperature for one hour. Ether, 20 ml, is added, and the mixture is stirred at 0° C. for one hour. Crystalline product is obtained by filtration.

Isobutylchloroformate, 2.72 ml plus 2 ml of DMF, is added to 2.6 g of pyroglutamic acid and 2.8 ml of triethylamine in 10 ml of DMF at −15° C., and the mixture is stirred at −15° C. for 10 minutes. HCl.Phe-trichlorophenyl ester, 7.62 g in 15 ml of DMF is added at −15° C, followed by the dropwise addition of 2.8 ml of triethylamine in 5 ml of DMF. The solution is stirred at −10° C for 1.5 hours and then at room temperature for one hour. Solvent is removed under high vacuum, and then 50 ml of cold ethyl acetate is added. The cold solution is washed until neutral. The desired compound is obtained by crystallization from ethyl acetate and hexane.

C. Preparation of 2-(<Glu—Phe—Arg)-Naphthylamide

Nα-Cbo-Arg-β-naphthylamide, 10 g, is converted to Arg-β-naphthylamide·2HBr by treatment with 30 ml of saturated HBr in acetic acid at room temperature for 45 minutes. The solution is treated with ether, and the solid product is collected by filtration and then dried in a vacuum desiccator.

<Glu-Phe-trichlorophenyl ester, 2.28 g, in 8 ml of DMF is added with stirring to Arg-β-naphthylamide·2HBr, 2.31 g, and 0.42 g of HaHCO₃ and 20 ml DMF and 10 ml of water. The solution is stirred at room temperature overnight. Solvent is removed under reduced pressure. The crude product is purified by silica gel column chromatography (CHCl₃/methanol/acetic acid, 95:5:3 by volume). The solvent of fractions containing the named compound is removed under reduced pressure, and the named compound is obtained by lyophilization from dilute acetic acid.

EXAMPLE 5

Synthesis of 2-(<Glu-Phe-Arg)-4-methoxy-naphthylamide

By substituting 2-amino-4-methoxynaphthalene for 2-amino naphthalene in Example 4, and repeating the procedure of Example 4, the named compound is obtained.

EXAMPLE 6

Synthesis of 5-(<Glu-Phe-Arg)-isophthalic acid dimethyl ester

By substituting 5-amino-isophthalic acid ester for 2-amino naphthalene in Example 4, and repeating the procedure of Example 4, the named compound is obtained.

EXAMPLE 7

Preparation of 7-(<Glu-Phe-Arg)-amido-4-methyl-coumarin hydrochloride

A. Synthesis of 7-(Nα-Cbo-Arg)-amido-4-methyl coumarin hydrochloride

DCC, 10.5 g in 10 ml of DMF, is added to 34.5 g of Nα-Cbo-Arg-HCl and 8.75 g of 7-amino-4-methyl-coumarin in 150 ml of DMF. The mixture is stirred at room temperature overnight and solid DCCU is removed by filtration. Solvent of the filtrate is reduced under high vacuum, and 25 ml of methanol and 250 ml of ethyl acetate is added. Crude product is collected by filtration. Crude product is dissolved in 15 ml of DMF plus 50 ml of methanol, and insoluble material is removed by filtration. Ethyl acetate, 200 ml, is added to the hot filtrate and the solution is allowed to stand at room temperature for several hours. Solid product is obtained by filtration.

B. Preparation of 7-(Nα-Cbo-Phe-Arg)-amido-4-methyl-coumarin

The product of step A of Example 7, 500 mg in methanol/acetic acid/H₂O, is deprotected by hydrogenation at 1 atmosphere for 3 hours using 5% Pd on carbon, 50 mg, as catalyst. The catalyst is removed by filtration, and solvent is removed under reduced pressure. The residue is triturated with ether to yield 7-(Arg)-amido-4-methyl-coumarin hemihydrate. A solution of the latter, 0.377 g in 10 ml of DMF and 10 ml of H₂O is mixed with 0.52 g of the N-OH-succinimide ester of Cbo-Phe in 2 ml of DMF. The mixture is stirred at room temperature overnight and then solvent is removed under reduced pressure. The crude product is purified by chromatography on silica gel (CHCl₃/methanol/acetic acid, 95:5:3 by volume).

C. Preparation of 7-(<Glu-Phe-Arg)-amido-4-methyl-coumarin hydrochloride

The product of step B of Example 7, 0.432 g in 30 ml of methanol is deprotected by hydrogenolysis (30 mg of 5% Pd on C, H₂ at 1 atmosphere for 3 hours). Catalyst is removed by filtration. Ether, 30 ml, is added to the filtrate to yield crystals. The crystals, 0.31 g dissolved in 3 ml of DMF, are mixed with 0.155 g of <Glu-trichlorophenyl ester in 1 ml of DMF. The mixture is stirred at room temperature overnight. Solvent is removed under high vacuum, and the crude product is purified by silica gel column chromatography.

EXAMPLE 8

Synthesis of 7-(<Glu-Phe-Arg)-amido-4-trifluoromethyl-coumarin

By substituting 7-amino-4-trifluoromethyl-coumarin for 7-amino-4-methyl coumarin in Example 7, and repeating the procedures of Example 7, the named compound is obtained.

EXAMPLE 9

Assay of human plasma kallikrein

Apparently pure plasma kallikrein or a 1/150 dilution of kaolin-activated plasma, both in 50 μl of 0.2 M Tris.HCl buffer, pH 8.0, 0.4% bovine serum albumin, was transferred to the bottom of a 12×75 mm disposable glass test tube. Blanks received 50 μl of assay buffer without enzyme. The reaction was begun by adding 50 μl of buffered <Glu—Phe—Arg-[$^3$H]benzylamide (0.1 uCi; 80 nM, 22 uCi/nmol). Reaction mixtures were incubated at 37° C. for 1-60 minutes and then the reactions were stopped by adding 1.0 ml of 0.1 N NaOH to each tube. Toluene, 1 ml, was added to each tube, and the contents were mixed by vortexing for 30 seconds.

The tubes were centrifuged at about 900 xg for 3 minutes. A sample, usually 500 μl, of the upper phase was transferred to a 7 ml liquid scintillation vial containing 5 ml of RIAfluor (New England Nuclear Corp.). A sample of the buffered substrate solution, 50 μl, was transferred to a scintillation vial containing the same liquid scintillation cocktail. Assay results were computed via the integrated form of the first order rate equation in units: One unit is the quantity of enzyme required to hydrolyze substrate at an initial rate of 1%/min. at 37° C. For any hydrolytic enzyme measured in this way, the units measured are equal to 100 Vmax/Km for a given quantity of enzyme [Cornish-Bowden, A. *Fundamentals of Enzyme-Kinetics* Butterworths London 1979, p. 23]. In this protocol, a small fraction of substrate is partitioned into the toluene phase. Most of the product, [$^3$H]benzylamine, is partitioned into the upper phase, but a constant fraction remains in the alkaline aqueous phase. Thus, the integrated form of the first order rate equation has been modified to $$[E] = 100(V\text{max}/Km) = \left[\frac{1}{kt}\right] \ln\left(\frac{S}{S - \left(\frac{(T-B)}{f_p - f_s}\right)}\right)$$

where [E]=enzyme activity, S is the initial substrate concentration in c.p.m., T is the c.p.m. of the test (unknown) upper phase, B is the c.p.m. of the blank (no enzyme) upper phase, $f_p$ is the fractional extraction of product into the upper phase, $f_s$ is the fractional extraction of substrate into the upper phase, k is 0.01 (to correct fractional substrate utilization into percent), and t is time of incubation in minutes. The expression $f_p-f_s$ is 0.7. Assay of apparently pure HPK with a variety of substrates, including <Glu—Phe—Arg-[$^3$H]benzylamide yielded data on the relative reaction rates given in the Table I below.

TABLE I

Relative Reaction Rates of Human Plasma Kallikrein with <Glu—Phe—Arg-[$^3$H]benzylamide and Related Substrates Table I shows the quantities of Human Plasma Kallikrein required in a 100 μl reaction volume to hydrolyze a given substrate at an initial rate of 1%/min at 37° C. The unit of 1%/min is equal to Vmax/Km×100.

TABLE I

Relative Reaction Rates of Substrate With HPK

| Substrate | HPK required (ng/unit) |
|---|---|
| <Glu—Phe—Arg—[$^3$H]benzylamide | 84 (8.4 nM) |
| (D)Phe—Phe—Arg—[$^3$H]benzylamide | 145 |
| Pec—Phe—Arg—[$^3$H]benzylamide | 146 |
| 4-keto-Pro—Phe—Arg—[$^3$H]benzylamide | 151 |
| Pro—Phe—Arg—[$^3$H]benzylamide | 995 |
| Cbo—Phe—Arg—[$^3$H]benzylamide | 1192 |
| Cpc—Phe—Arg—[$^3$H]benzylamide | 1532 |
| Acetyl-Phe—Arg—[$^3$H]benzylamide | 1958 |
| (D)Pro—Phe—Arg—[$^3$H]benzylamide | 2229 |
| Bz—Phe—Arg—[$^3$H]benzylamide | 13398 |
| Phe—Arg—[$^3$H]benzylamide | (no hydrolysis) |

While the invention has been described in connection with specific embodiments thereof, it will be understood that it is capable of further modifications and this application is intended to cover any variations, uses, or adaptations of the invention following, in general, the principles of the invention and including such departures from the present disclosure as are known to one of ordinary skill in the art to which the invention pertains and as may be applied to the essential features hereinbefore set forth, and as follows in the scope of the appended claims.

What is claimed is:

1. Novel compounds of the general formula:

A—L—phe—L—arg—Y, or methyl esters thereof or ethyl esters thereof, wherein,
group A contains a carbonyl moiety in amide linkage with the α-amino group of L—Phe and is any one of the groups consisting essentially of cyclopropanecarbonyl, cyclobutanecarbonyl, cyclopentanecarbonyl, cyclohexanecarbonyl, pyroglutamyl, 3,4-dehydroprolyl, 4-ketoprolyl, 4-OH-prolyl, 3-OH-prolyl, 3-phenylpropanoyl, thioprolyl, azetidine-2-carbonyl, thiazolidine-4-carbonyl, 5-X-prolyl, 4-X-prolyl, 3-X-prolyl, and 2-X-prolyl wherein X of any of the last four radicals is halo; and
group Y is joined to the α-carbonyl of L—Arg to form an ester or amide linkage therewith and is —OH or any known indicator that is radioactively or chemiluminescently tagged or which comprises a chromogen or fluorogen except that when A is pyroglutamyl Y is a radioactively or chemiluminescently tagged benzylamide group.

2. A compound according to claim 1 wherein A is not pyroglutamyl and Y is a radioactively tagged group and is any one of the group consisting essentially of [$^3$H]-anilino, [$^3$H]-benzylamino, [$^{14}$C]-anilino, [$^{14}$C]-benzylamino, [$^3$H]-methoxy, [$^3$H]-ethoxy, [$^{14}$C]-methoxy, [$^{14}$C]-ethoxy, 4-Z-naphthyl-2-amino, 4-Z-naphthyl-1-amino, Z-hydroxyanilino, Z-hydroxybenzylamino and 5-Z-coumaryl-7-amino, wherein Z is a radioactive halogen.

3. A compound according to claim 1 wherein A is not pyroglutamyl and Y is a chromogenic tag and is any one of the group consisting essentially of p-NO$_2$-anilino, p-NO$_2$-phenyloxy, nitrophenylamino, naphthylamino, nitronaphthylamino, methoxynaphthylamino, quinolylamino, nitroquinolylamino, 4-trifluoromethyl coumaryl-7-amino, 4-Z-naphthyl-1-amino and 4-Z-naphthyl-2-amino, wherein Z is radioactive halogen.

4. A compound according to claim 1 wherein A is not pyroglutamyl and Y is a fluorogenic tag and is any one of the group consisting essentially of 4-methyl coumaryl-7-amino, 4-trifluoromethyl coumaryl-7-amino, naphthylamino, 7-oxy-coumaryl, 5-amino isophthallic acid dimethyl ester, 5-Z coumaryl-7-amino, 4-Z-naphthyl-1-amino and 4-Z-naphthyl-2-amino, wherein Z is a radioactive tag.

5. A compound according to claim 1 wherein Y is a chemiluminescent tag and is amino-iso-luminol.

6. A compound according to claim 1 wherein Y is a radioactively tagged group and is any one of the group consisting essentially of [$^3$H]-anilino, [$^3$H]-benzylamino, [$^{14}$C]-anilino and [$^{14}$C]-benzylamino.

7. A compound according to claim 1 wherein A is not pyroglutamyl and Y is a chromogenic tag and is either of the group consisting of p-NO$_2$-anilino and 2-naphthylamino.

8. A compound according to claim 1 wherein A is not pyroglutamyl and Y is a fluorogenic tag and is either of the group consisting of 4-methyl coumaryl-7-amino and 4-trifluoromethyl coumaryl-7-amino.

9. A compound according to claim 1 wherein A is any of the group consisting essentially of 3-phenyl propanoyl and 4-keto prolyl.

10. A compound according to claim 1 wherein,
group A is 3-phenylpropanoyl or 4-keto prolyl;
when group Y is a radioactively tagged group, Y is any one of the group consisting essentially of [$^3$H]-anilino, [$^3$H]-benzylamino, [$^{14}$C]-anilino, and [$^{14}$C]-benzylamino;
when Y is a chromogenic tag, Y is either of p—NO$_2$-anilino and 2-naphthylamino;
when Y is a fluorogenic group, Y is either of 4-methyl coumaryl-7-amino and 4-trifluoromethyl coumaryl-7-amino;
when Y is chemiluminescent, Y is amino isoluminol.

11. A compound according to claims 1, 2, 3, 4, 5, 6, 7, 8, 9, or 10 wherein Y is [$^3$H]-benzylamino.

12. A compound according to claim 1 wherein A is pyroglutamyl and Y is [$^3$H]-benzylamino.

13. A compound according to claim 1 wherein A is phenylpropanoyl and Y is [$^3$H]benzyl.

14. A compound according to claim 1 wherein A is 4-ketoprolyl and Y is [$^3$H]-benzylamino.

* * * * *